United States Patent
Cecchi et al.

(10) Patent No.: US 11,925,734 B2
(45) Date of Patent: Mar. 12, 2024

(54) AIR PURIFICATION SYSTEM

(71) Applicants: Paige E. Cecchi, Longboat Key, FL (US); Michael D. Cecchi, Longboat Key, FL (US)

(72) Inventors: Paige E. Cecchi, Longboat Key, FL (US); Michael D. Cecchi, Longboat Key, FL (US)

(*) Notice: Subject to any disclaimer, the term of this patent is extended or adjusted under 35 U.S.C. 154(b) by 383 days.

(21) Appl. No.: 17/240,145

(22) Filed: Apr. 26, 2021

(65) Prior Publication Data

US 2022/0339312 A1 Oct. 27, 2022

(51) Int. Cl.
*A61L 9/14* (2006.01)
*A61L 9/20* (2006.01)

(52) U.S. Cl.
CPC .............. *A61L 9/14* (2013.01); *A61L 9/20* (2013.01); *A61L 2209/111* (2013.01); *A61L 2209/134* (2013.01); *A61L 2209/14* (2013.01); *A61L 2209/211* (2013.01)

(58) Field of Classification Search
CPC ........ A61L 9/14; A61L 9/20; A61L 2209/111; A61L 2209/134; A61L 2209/14; A61L 2209/211
See application file for complete search history.

(56) References Cited

U.S. PATENT DOCUMENTS

| | | | |
|---|---|---|---|
| 2017/0112954 A1* | 4/2017 | Dayton | ............ A61L 9/20 |
| 2021/0346120 A1* | 11/2021 | Roberts | ............ A61L 9/20 |

* cited by examiner

*Primary Examiner* — Sean E Conley
*Assistant Examiner* — Brendan A Hensel
(74) *Attorney, Agent, or Firm* — Michael A. Blake

(57) ABSTRACT

An air purification system configured to have a flow of air through a first air purification device from ambient air, through an inlet vent into an enclosure, then through a filter, then through a blower, then through UV light rays emanating from a UV light source, then through a spray of disinfectant from at least one disinfectant sprayer, then through a second filter, then out of the enclosure through an outlet vent back into the ambient air.

11 Claims, 2 Drawing Sheets

AIR PURIFICATION SYSTEM

TECHNICAL FIELD

The present invention relates generally to air purification systems, and more particularly, air purification systems that can receive air from the top of an apparatus and expel clean air from the bottom of the apparatus.

BACKGROUND

Currently there are many variations of air filtration and purification devices in use and in the marketplace. All use similar system of filters and blower motors to circulate the air within an environment. If the unit is a freestanding unit, they draw the air in through the bottom of the unit and disperse the air out of the top of the unit, to disperse the air throughout the environment. This system seems to be adequate to remove particulates and dust from the environment.

But, with the advent and spread of the deadly Corona Virus 19, the circumstance and dangers has changed, and has created a drastic change to the needs of this equipment and the performance outcome.

The problem with the current devices is that if the Corona Virus 19 is in the air of the environment, it may actually be spread through the room, by being pushed 'in front' of or ahead of the air that is being expelled from the unit, as most units expel the air upward and throughout the room. It would therefore be spreading the virus germs throughout the environment. The units rely on pulling in the air at the bottom of the unit, through the air must circulate the room and then be brought back into the base of the unit.

Another problem facing current devices is that they are not mobile, and may not cover the environment as needed.

Another problem, facing the current devices, is that there is no coordinated method of fully cleaning the environment.

It would be highly desirable to make an air filtration and purification unit which will remove the particulates and contaminants within the air, and to be able kill and help eliminate the Corona 19 virus.

Thus there is a need for an air purification system that overcomes the above listed and other disadvantages.

SUMMARY OF THE INVENTION

The invention relates to an air purification system, the air purification system comprising: a first air purification device, the first air purification device comprising: an enclosure, the enclosure comprising a top, sides, and bottom; an inlet vent located at or near the top of the enclosure; a first filter located in the enclosure and below the inlet vent; a blower located in the enclosure and below the first filter; at least one UV light source located inside the enclosure below the blower; at least one disinfectant sprayer located inside the enclosure below the blower; a second filter located in the enclosure, and below the UV light source and the sprayer; an outlet vent located below the second filter and at or near the bottom of the enclosure; a control center located on the enclosure, the control center comprising: a battery, a computing device in communication with a network; a navigation system in communication with the computing device; a camera in communication with the computing device; a moveable arm located on the enclosure, the moveable arm in communication with the computing device; an air sensor located on the rotatable arm, the air sensor in communication with the computing device; a plurality of wheels attached to the enclosure and configured to move the first air purification device; a motor in communication with one or more of the plurality of wheels, the motor in communication with the computing device; where when the air purification system is activated, the flow of air through the first air purification device is from the ambient air, through the inlet vent into the enclosure, then through the first filter, then through the blower, then through UV light rays emanating from the UV light source, then through a spray of disinfectant from the at least one disinfectant sprayer, then through the second filter, then out of the enclosure through the outlet vent back into the ambient air.

BRIEF DESCRIPTION OF THE DRAWINGS

The present disclosure will be better understood by those skilled in the pertinent art by referencing the accompanying drawings, where like elements are numbered alike in the several figures, in which.

DETAILED DESCRIPTION OF THE INVENTION

The invention is a device for the air purification and disinfecting system where autonomous units are coordinated or 'teamed.' The air filtration and cleaning devices may work independently and as a team to help purify and disinfect an enclosed environment. The invention is self-propelled and is able to move within an environment, collect data, with aid of one or more sensors, as to air quality, levels and types of contaminants. The units are autonomous and may work together with a control center.

The invention is an air purification system that works autonomously to clean the air within an indoor space and to clean the environment. In other embodiments, the air purification system can work with other air purification system units to clean an indoor space. The mission is to kill and help control, bacteria and virus, the novel Coronavirus-19, and other pathogens, with a series or team of device, real-time communication between the device, mapping of the environment and a very effective disincentive system for optimum performance and outcome.

One embodiment of the invention is an air purification device and virus elimination system. It contains, filters, blowers, fluids, disinfectants and is able to travel. It may be made of several material, such as plastic or metals, may range in height from about 3 feet to 8 feet tall. The device may use a down draft of the incoming air, taking air from a higher point in the room and bringing the air towards the floor. The unit may be on wheels, portable, may be battery powered. The unit may include sensor equipment, cameras, and be equipped with GPS. It may be driven by an operator, viewing the environment through the on-board cameras. Alternatively, it may use artificial intelligence to determine where to travel in the indoor environment to provide air filtration.

Figure 1:
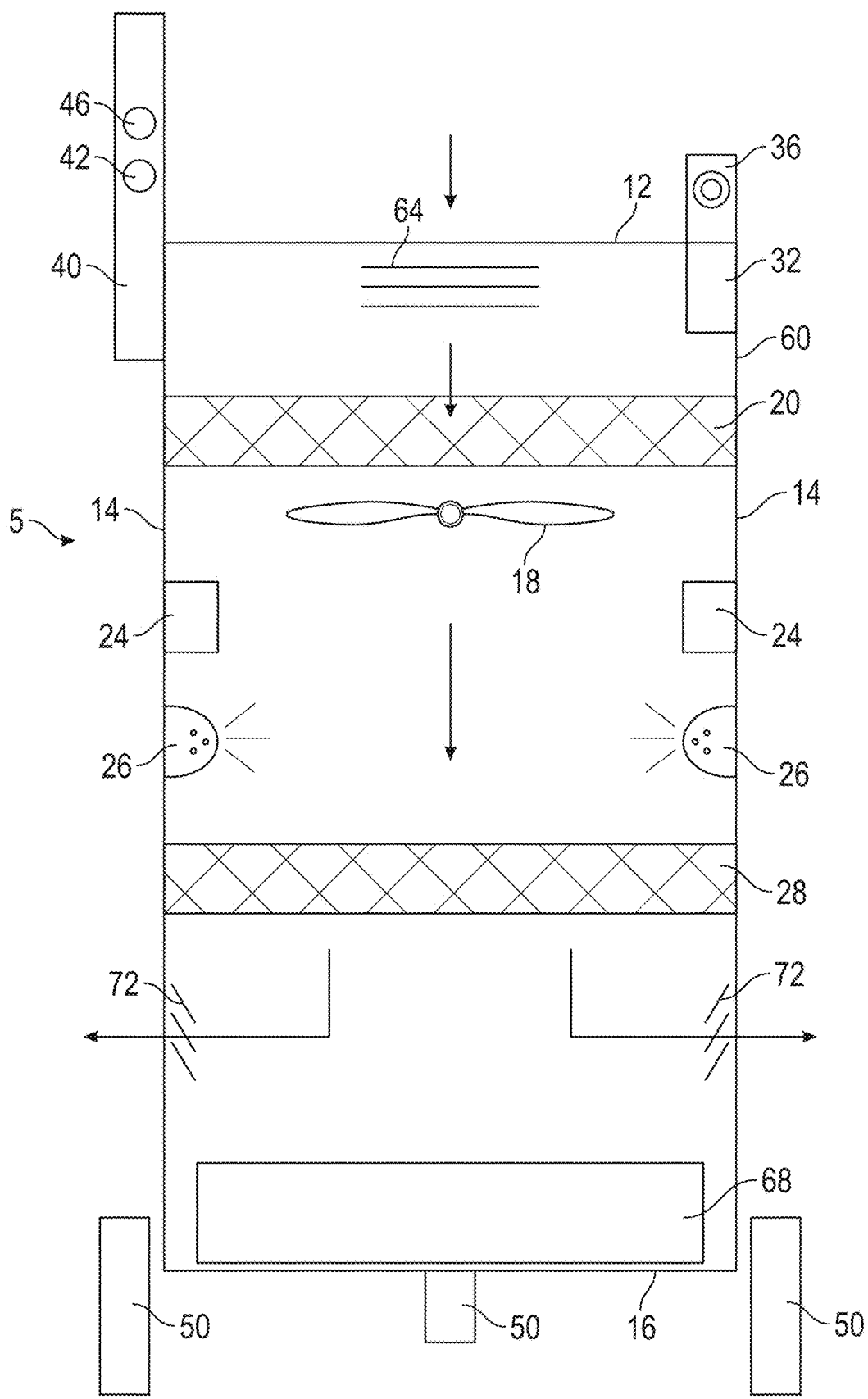
FIG. 1 is a front view of the air purification device.

FIG. 1, shows an embodiment of the air purification system 5. The system 5 comprises and air purification device 10, with an enclosure 60 comprising a top 12, sides 14 and a bottom 16. The device 10 may take air flow through the top vents 64, and pull the air into the enclosure 60 by a blower 18. The blower directs the air in a downward direction through a first filter 20. The first filter 20 may be a HEPA filter. HEPA filters will remove about 99.997% of particulates, viruses and such from the air. Any remaining toxins which pass through the first filter 20 are then subjected to UV light rays from a UV light source 24 and a disinfectant sprayed from sprayers 26. The use of the first filter 20 on the air will make the UV light rays and disinfectant to be more effective in cleaning the air.

The UV light source 24 may include UV lights and/or UV-C lights. The disinfectant may be a series of liquid or misting sprays of disinfectant which will further clean the air and/or kill any viruses. The disinfectant may contain alcohol, bleaches and proprietary mixtures. Next, the air flows through a second filter 28. The second filter 28 may comprise a filter material or fiber material. The second 28 filter may have a rating from about Merv 4 to about Merv 10. In other embodiments, the second filter 28 may also comprise a disinfectant in the filter or fiber material to assist in killing any viruses, bacterias or other deleterious organisms. The liquid disinfectant may be collected in a liquid container 68. The container 68 may be removable and replaceable in the air purification device 10.

The device 10 may include a control center 32. The control center 32 may comprise a battery, GPS/navigation system, a computing device, and the control center 32 may be in communication with a network. A camera 36 may also be in communication with the control center. The camera 36 may be rotatable and moveable with respect to the enclosure 60. Throughout this patent application, numerous references may be made regarding servers, services, engines, modules, interfaces, portals, platforms, or other systems formed from computing devices. It should be appreciated that the use of such terms are deemed to represent one or more computing devices having at least one processor configured to or programmed to execute software instructions stored on a computer readable tangible, non-transitory medium. For example, a server can include one or more computers operating as a web server, database server, or other type of computer server in a manner to fulfill described roles, responsibilities, or functions. Within the context of this document, the disclosed smart phones, tablets, or hand held computers are also deemed to comprise computing devices having a processor and a non-transitory memory storing instructions executable by the processor that cause the device to control, manage, or otherwise manipulate the features of the disclosed apparatuses, systems and methods. The network may be or include the Internet, World Wide Web, a local area network, or some other public or private computer, cable, telephone, cellular telephone system, client/server, peer-to-peer, or communication network or intranet. In some embodiments, the communication network can also include other public and/or private wide area networks, local area networks, wireless networks, data communications networks, or connections, intranets, routers, satellite links, microwave links, cellular or telephone networks, radio links, fiber optic transmission lines, ISDN lines, T1 lines, DSL connections, etc.

The device 10 may comprise a moveable arm 40. The arm 40 may swivel and turn. The arm may comprise an air sensor 42 for the analyses of the room air for contaminants and such, be able to analyses and monitor the incoming air for pollutants and to analyze report and react to this data information, communicating with the other devices and reacting accordingly. The arm may also comprise a camera 46. The camera 46 may be used to taking images and sending images, as well as allowing the device to be remotely driven.

The device may be in height from about 3 feet tall to 8 feet tall. One embodiment may be about 6 and 7 feet tall, allowing it work in a normal height room of eight feet and doorways. The device may comprise 2 or more wheels 50. The wheels may be powered or motorized and in communication with the control center 32.

The invention device may be battery powered and able to return to the 'bench', a recharging station, (not shown) for the device 10. This recharging station may be configured to recharge the system's batteries, adding disinfectant to the sprayers 26, and to remove the liquid in the liquid container 68. The device 10 may be battery powered, or may be powered by plugging into the building's electrical system. If battery powered, the air purification device 10 will be better suitable for travel within a room or building.

The disclosed air purification device 10 has the air incoming on the top 12 of the enclosure 60, driven by a blower 18. The air is cleaned by a first filter 20, which may be a HEPA filter, then the air is directed down past UV light sources 24 to help kill the germs and viruses. Next, the air passes by sprayers 26 which spray disinfectant which is designed to kill viruses, germs and other contaminants, including but not limited to the deadly novel Corona 19 virus and the like. The disinfectant may have a disinfectant grade, and may comprise alcohol, hydrogen peroxide and bleaches, or a proprietary fluid created for the device. The air will then go through a second filter 28, which may be a light rated filter, which will generally retain the sprayed disinfectant and may apply additional disinfectants as the air passes through the second filter 28. The air is directed out of the enclosure 60 through the bottom vents 72 into the room. Used liquid disinfectant may be collected in the liquid container 68.

The device 10 may be self-propelled and able to move and roam the environment while using its air sensor 42, such as an on-board pollution detecting device, and GPS. Using data from the air sensor and GPS, the device 10 can go to locations with higher levels of pollution, dirty air, viruses, bacteria, and clean the air in those areas. The device 10 may also create a map of the environment it is located in, and assign values of pollution for different locations in the environment. The device 10 may be used in concert with other devices 10, which may communicate with each other through a network, in order to efficiently clean the air in the environment by having the multiple devices 10 go to different areas to clean the air.

The device 10 may be self-propelled and may be driven remotely from a central control center. In one example the device the device is self-propelled and may be driven remotely, this driving feature, will enable the device 10 to enter Corona Virus 19 areas and disinfect them, without the danger of exposing a person to the Corona Virus or other pathogen. The driving feature may allow the device 10 and remote driver to map the environment without exposure to pathogens or dirty air. This feature will work well for patients coming home from a hospital, and the device 10 can clean the air prior to the patient entering his or her home. The device 10 will be able to map new areas, and assign problem areas where more air cleaning may be necessary.

These devices 10 may be used autonomously or in with other devices 10 in a particular environment. The device 10 will be able to move thru and roam the environment while, using the air sensor 42 (also known as an on-board pollution detecting device), and direct its attention to the cleaning the air in locations with high levels of pollution or pathogens detected. The device 10 may be able to release or spray a disinfectant mist into determined areas to help kill the virus, or other pathogens. The device 10 may be used with multiple similar or compatible units, communicating real-time with other devices and directing these devices to better control the environment.

Figure 2:
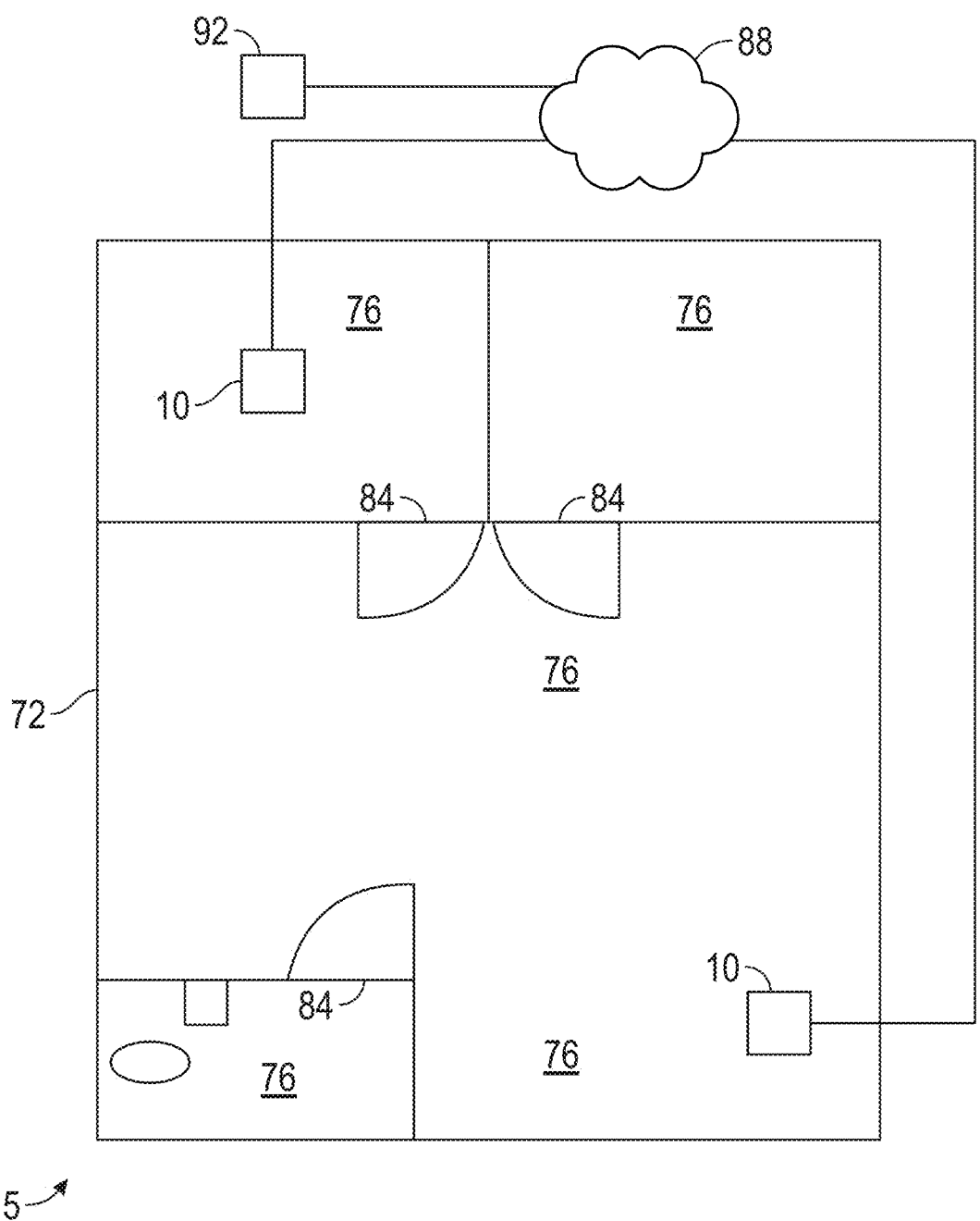
FIG. 2 is a schematic view of the system.

FIG. 2 shows an embodiment of the air purification system 5. The system 5 may comprise one or more air purification devices 10. The devices may be located in an interior environment 72. The interior environment may include, but is not limited to, a business, a home, offices, warehouse, laboratory, etc. The interior environment 72 may comprise rooms 76, and walls 80, and doorways 84. Each of the devices 10 may be in communication with a network 88, such as an internet or intranet. A main computing device 92 may be in communication with the network, and may store data from the devices 10. The main computing device 92 may be remotely located from the air purification devices, and may control the actions and movement of the individual air purification devices. In other embodiments, the devices themselves may store all the data. The devices 10 may coordinate with each other via the network 88 to configure a cleaning route each device 10 may take in the environment 72 to efficiently clean the air in the environment. The devices 10 may create a map of the environment, to maximize efficiency of the devices 10 travelling throughout the environment 72.

The disclosed air purification system and device has many advantages. It cleans the air in at least 4 ways, with 2 filters, UV light, and disinfectant spray. The device can independently move about an environment to clean locations that have greater amounts of pathogens or otherwise dirty air. The device can communicate with other devices to efficiently clean an environment, by having the devices spread out and clean different areas of an environment at the same time. The device can collected used disinfectant which can be emptied from a liquid container. The device has an air sensor, where it can measure the amount of pathogens or pollutions in the air, and map that information with respect to its environment, and keep data on who the amount of pollution and/or pathogens change over time, so that the device can clean areas of the environment in anticipation of when those areas will develop higher levels of pollution and/or pathogens. The device may have a camera to allow a remote driver to operate the device.

It should be noted that the terms "first", "second", and "third", and the like may be used herein to modify elements performing similar and/or analogous functions. These modifiers do not imply a spatial, sequential, or hierarchical order to the modified elements unless specifically stated.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for carrying out this disclosure, but that the disclosure will include all embodiments falling within the scope of the appended claims.

What is claimed is:

1. An air purification system, the air purification system comprising:
 a first air purification device, the first air purification device comprising:
  an enclosure, the enclosure comprising a top, sides, and bottom;
  an inlet vent located at about the top of the enclosure;
  a first filter located in the enclosure and below the inlet vent;
  a blower located in the enclosure and below the first filter;
  at least one UV light source located inside the enclosure below the blower;
  at least one disinfectant sprayer located inside the enclosure below the blower;
  a second filter located in the enclosure, and below the UV light source and the sprayer;
  an outlet vent located below the second filter and at or near the bottom of the enclosure;
  a control center located on the enclosure, the control center comprising:
   a battery,
   a computing device in communication with a network;
   a navigation system in communication with the computing device;
   a camera in communication with the computing device;
  a moveable arm located on the enclosure, the moveable arm in communication with the computing device;
  an air sensor located on the movable arm, the air sensor in communication with the computing device;
  a plurality of wheels attached to the enclosure and configured to move the first air purification device;
  a motor in communication with one or more of the plurality of wheels, the motor in communication with the computing device;
 wherein when the air purification system is activated, the flow of air through the first air purification device is from the ambient air, through the inlet vent into the enclosure, then through the first filter, then through the blower, then through UV light rays emanating from the UV light source, then through a spray of disinfectant from the at least one disinfectant sprayer, then through the second filter, then out of the enclosure through the outlet vent back into the ambient air.

2. The air purification system of claim 1, wherein the first filter is a HEPA filter and the second filter has a rating of about Merv 4 to about Merv 10.

3. The air purification system of claim 1, wherein the disinfectant comprises alcohol.

4. The air purification system of claim 1, wherein the disinfectant comprises hydrogen peroxide.

5. The air purification system of claim 1, wherein the disinfectant comprises bleach.

6. The air purification system of claim 1, the air purification system further comprising:
 a main computing device in communication with the network;
 a second air purification device, the second air purification device comprising:
  an enclosure, the enclosure comprising a top, sides, and bottom;
  an inlet vent located at about the top of the enclosure;
  a first filter located in the enclosure and below the inlet vent;
  a blower located in the enclosure and below the first filter;
  at least one UV light source located inside the enclosure below the blower;
  at least one disinfectant sprayer located inside the enclosure below the blower;
  a second filter located in the enclosure, and below the UV light source and the sprayer;
  an outlet vent located below the second filter and at or near the bottom of the enclosure;

a control center located on the enclosure, the control center comprising:
a battery,
a computing device in communication with a network;
a navigation system in communication with the computing device;
a camera in communication with the computing device;
a moveable arm located on the enclosure, the moveable arm in communication with the computing device;
an air sensor located on the movable arm, the air sensor in communication with the computing device;
a plurality of wheels attached to the enclosure and configured to move the second air purification device;
a motor in communication with one or more of the plurality of wheels, the motor in communication with the computing device;
wherein when the air purification system is activated, the flow of air through the second air purification device is from the ambient air, through the inlet vent into the enclosure, then through the first filter, then through the blower, then through UV light rays emanating from the UV light source, then through a spray of disinfectant from the at least one disinfectant sprayer, then through the second filter, then out of the enclosure through the outlet vent back into the ambient air;
and the computing device of the first air purification device, the computing device of the second air purification device are in communication with the main computing device, and the main computing device controls the movement and actions of the first air purification and the second air purification device.

7. The air purification system of claim 6, wherein the main computing device collects data from the first and second air purification devices, and directs the first and second air purification to move and clean the air based on the data received by the main computing device.

8. The air purification system of claim 7, wherein the main computing device develops a map to direct the movement and actions of the first and second air purification devices.

9. The air purification system of claim 1, where the enclosure is about 8 feet tall, and the inlet vent is about 7 feet above the ground.

10. The air purification system of claim 1, where the enclosure is about 7 feet tall, and the inlet vent is about 6 feet above the ground.

11. The air purification system of claim 1, where the enclosure is about 3 feet tall.

* * * * *